(12) United States Patent
Hall

(10) Patent No.: US 9,851,982 B2
(45) Date of Patent: Dec. 26, 2017

(54) EMERGENCY VIDEO CAMERA SYSTEM

(71) Applicant: Stewart E. Hall, Wellington, FL (US)

(72) Inventor: Stewart E. Hall, Wellington, FL (US)

(73) Assignee: Tyco Fire & Security GmbH, Neuhausen am Rheinfall (CH)

( * ) Notice: Subject to any disclaimer, the term of this patent is extended or adjusted under 35 U.S.C. 154(b) by 82 days.

(21) Appl. No.: 14/463,877

(22) Filed: Aug. 20, 2014

(65) Prior Publication Data

US 2015/0249787 A1    Sep. 3, 2015

Related U.S. Application Data

(60) Provisional application No. 61/973,962, filed on Apr. 2, 2014, provisional application No. 61/946,054, filed on Feb. 28, 2014.

(51) Int. Cl.
*H04N 5/232*    (2006.01)
*G06F 9/44*    (2006.01)
(Continued)

(52) U.S. Cl.
CPC ............ *G06F 9/4416* (2013.01); *A61B 17/00* (2013.01); *G01S 5/02* (2013.01); *G01S 5/0236* (2013.01); *G01S 5/0284* (2013.01); *G01S 13/765* (2013.01); *G06F 8/63* (2013.01); *G08B 7/062* (2013.01); *G08B 7/066* (2013.01); *G08B 13/19613* (2013.01); *G08B 13/19697* (2013.01); *H04L 9/004* (2013.01); *H04L 12/4625* (2013.01); *H04L 12/6418* (2013.01); *H04L 43/0876* (2013.01); *H04L 61/106* (2013.01); *H04L 67/12* (2013.01); *H04L 67/34* (2013.01); *H04N 5/23241* (2013.01); *H04N 5/76* (2013.01);
(Continued)

(58) Field of Classification Search
CPC ..... G06F 9/4416; G06F 8/63; H04L 12/6418; H04L 12/4625; H04L 43/0876; H04L 43/10; H04N 5/76; H04N 5/23241; H04W 24/02; H04W 16/26
USPC ............................................. 348/333.13, 372
See application file for complete search history.

(56) References Cited

U.S. PATENT DOCUMENTS 5,406,327 A    4/1995 Guarnotta
6,741,165 B1   5/2004 Langfahl et al.
(Continued)

FOREIGN PATENT DOCUMENTS

| WO | WO 01/06401   | 1/2001  |
|----|---------------|---------|
| WO | WO 2004/068855 | 12/2004 |
| WO | WO 2013/159217 | 10/2013 |

OTHER PUBLICATIONS

International Search Report and Written Opinion, PCT/US15/17680.
International Search Report and Written Opinion, PCT/US15/17688.
International Search Report and Written Opinion, PCT/US15/17702.

*Primary Examiner* — Padma Haliyur
(74) *Attorney, Agent, or Firm* — Fish & Richardson P.C.

(57) ABSTRACT

A surveillance system includes one or more camera systems at least some of the camera systems including a camera element comprising optical components to capture and process light to produce images, camera processing circuitry that receives the light and processes the into electrical signals and encodes the signals into a defined format, power management circuitry to power the camera system, the power management system including first and second power interfaces and first and second video output interfaces.

19 Claims, 6 Drawing Sheets

(51) Int. Cl.

| | | |
|---|---|---|
| *G06F 9/445* | (2006.01) | |
| *H04L 12/46* | (2006.01) | |
| *H04L 12/26* | (2006.01) | |
| *H04N 5/76* | (2006.01) | |
| *H04W 16/26* | (2009.01) | |
| *H04W 24/02* | (2009.01) | |
| *H04L 12/64* | (2006.01) | |
| *H04L 29/08* | (2006.01) | |
| *H04L 29/12* | (2006.01) | |
| *A61B 17/00* | (2006.01) | |
| *G01S 5/02* | (2010.01) | |
| *G01S 13/76* | (2006.01) | |
| *G08B 7/06* | (2006.01) | |
| *G08B 13/196* | (2006.01) | |
| *H04L 9/00* | (2006.01) | |
| *H04W 8/26* | (2009.01) | |
| *G08B 25/00* | (2006.01) | |
| *H04W 92/02* | (2009.01) | |

(52) U.S. Cl.
CPC ............ *H04W 8/26* (2013.01); *H04W 16/26* (2013.01); *H04W 24/02* (2013.01); *G08B 13/19671* (2013.01); *G08B 25/007* (2013.01); *G08B 25/009* (2013.01); *H04L 43/0805* (2013.01); *H04L 61/6013* (2013.01); *H04L 61/6072* (2013.01); *H04W 92/02* (2013.01); *Y04S 40/168* (2013.01)

(56) References Cited

U.S. PATENT DOCUMENTS

| | | |
|---|---|---|
| 6,757,008 B1 | 6/2004 | Smith |
| 6,812,970 B1 | 11/2004 | McBride |
| 6,924,732 B2 | 8/2005 | Yokoo |
| 7,525,594 B2 | 4/2009 | Tatamiya et al. |
| 8,115,862 B2 | 2/2012 | Umeyama et al. |
| 8,207,814 B2 * | 6/2012 | Biles ............... G07C 9/00571 340/5.2 |
| 8,633,829 B2 | 1/2014 | Cavanaugh |
| 8,670,873 B2 | 3/2014 | Shloush et al. |
| 8,711,197 B2 | 4/2014 | Dickerson et al. |
| 8,723,972 B2 | 5/2014 | Hinkel et al. |
| 8,750,513 B2 | 6/2014 | Renkis |
| 8,752,106 B2 | 6/2014 | Renkis |
| 2004/0109059 A1 | 6/2004 | Kawakita |
| 2006/0022816 A1 | 2/2006 | Yukawa |
| 2007/0239350 A1 | 10/2007 | Zumsteg et al. |
| 2008/0068267 A1 | 3/2008 | Huseth |
| 2009/0021634 A1 | 1/2009 | Chang |
| 2011/0051656 A1 | 3/2011 | Hethuin et al. |
| 2011/0310791 A1 | 12/2011 | Prakash et al. |
| 2013/0003645 A1 | 1/2013 | Shapira et al. |
| 2013/0041646 A1 * | 2/2013 | Farley ................ G08B 25/14 704/2 |
| 2013/0064233 A1 | 3/2013 | Hethuin et al. |

\* cited by examiner

EMERGENCY VIDEO CAMERA SYSTEM

CLAIM OF PRIORITY

This application claims priority under 35 U.S.C. §119(e) to provisional U.S. Patent Application 61/973,962, filed on Apr. 2, 2014, entitled: "Wireless Sensor Network", and provisional U.S. Patent Application 61/946,054, filed on Feb. 28, 2014, entitled: "Wireless Sensor Network", the entire contents of which are hereby incorporated by reference.

BACKGROUND

This description relates to operation of security and surveillance systems.

It is common for businesses and homeowners to have a security system for detecting alarm conditions at their premises and signaling the conditions to a monitoring station or to authorized users of the security system. Security systems often include an intrusion detection panel that is electrically or wirelessly connected to a variety of sensors. Those sensors types typically include motion detectors, cameras, and proximity sensors (used to determine whether a door or window has been opened).

SUMMARY

Traditional surveillance video camera systems have been designed for normal modes of operation within a building when power is available. In a typical traditional video surveillance system the components of the video camera system draw power from the building power. This is normally not a problem because building power is generally very reliable and can even be backed up by back-up generators.

During emergency situations, particularly when it involves fire or the chance of explosions, emergency responders generally turn off the building power. Fire Detection systems are designed to provide building power to the emergency evacuation system that provides occupants notification of the emergency, emergency lighting and notification appliances that provide audible instructions for evacuation.

One of the major limitations of traditional video systems that are not on battery back-up is that as soon as the building power is shut off, there is no availability of video images (still or continuous) to "look-in" to help monitor the state of an evacuation, to look for smoke or fire, or to look into areas where people may be trapped.

According to an aspect, a camera system includes a camera including optical components to capture and process optical energy to produce images, camera processing circuitry that receives the optical energy and processes the optical energy into electrical signals and encodes the signals into a defined format and power management circuitry to power the camera system. The power management system includes a first power interface, a second, different power interface, and circuitry to switch from the first power interface to the second power interface upon detection of loss or imminent toss of power from the first interface.

The following are some embodiments within the scope of the aspect.

The system includes a video local storage device. The system includes a local power storage device. The first power interface is a normal power operation interface that is configured to connect to normal building power and the second power interface is an emergency power input interface that is configured to connect to a fire panel. The system includes a first video output interface and a second different video output interface.

According to an additional aspect, a camera system includes a camera comprising optical components to capture and process light to produce video, camera processing circuitry that receives the light and processes the light into electrical signals and encodes the signals into a defined format and power management circuitry to manage power for the camera system. The power management system includes a first video output interface and a second different video output interface.

The following are some embodiments within the scope of the aspect.

The system includes a video local storage device. One of the first and second output interfaces comprises circuitry for providing a wireless network connection. The first video output interface is a normal video output interface and the second video output interface is an emergency video output interface.

According to an aspect, a surveillance system includes one or more camera systems at least some of the camera systems including a camera element including optical components to capture and process light to produce images, camera processing circuitry that receives the light and processes the light into electrical signals and encodes the signals into a defined format and power management circuitry to power the camera system. The power management system includes a first power interface, a second, different power interface; and circuitry to switch from the first power interface to the second power interface upon detection of loss or imminent loss of power from the first interface. The system also includes a first video output interface and a second different video output interface.

The following are some embodiments within the scope of the aspect.

The first interface is a normal power operation interface that is configured to connect to normal building power and the second interface is an emergency power input interface that is configured to connect to a fire panel. The first output interface is an emergency output interface and the second output interface is a normal output interface. The first interface is a local power storage element that supplies power to the camera only during emergencies. The local power storage element is fed by a power harvesting element that supplies power to the local storage element. The local power storage element is fed by building power. The system includes sensor nodes and a wireless sensor network to couple the one or more video cameras to monitors and the sensor nodes to monitoring units.

Described is a video surveillance system including an emergency video camera and system that allows access to video information for operation during a power and communication outage by use of a backup power network provided by a fire notification system.

The details of one or more embodiments of the invention are set forth in the accompanying drawings and the description below. Other features, objects, and advantages of the invention is apparent from the description and drawings, and from the claims.

DETAILED DESCRIPTION

Described herein are examples of emergency cameras having features that may be used in various contexts including, but not limited to, security/intrusion and alarm systems. Example security systems may include an intrusion detection panel that is electrically or wirelessly connected to a variety of sensors. Those sensors types may include motion detectors, cameras, and proximity sensors (used, e.g., to determine whether a door or window has been opened). Typically, such systems receive a relatively simple signal (electrically open or closed) from one or more of these sensors to indicate that a particular condition being monitored has changed or become unsecure.

For example, typical intrusion systems can be set-up to monitor entry doors in a building. When a door is secured, a proximity sensor senses a magnetic contact and produces an electrically closed circuit. When the door is opened, the proximity sensor opens the circuit, and sends a signal to the panel indicating that an alarm condition has occurred (e.g., an opened entry door).

Data collection systems are becoming more common in some applications, such as home safety monitoring. Data collection systems employ wireless sensor networks and wireless devices, and may include remote server-based monitoring and report generation. As described in more detail below, wireless sensor networks generally use a combination of wired and wireless links between computing devices, with wireless links usually used for the lowest level connections (e.g., end-node device to hub/gateway). In an example network, the edge wirelessly-connected) tier of the network is comprised of resource-constrained devices with specific functions. These devices may have a small-to-moderate amount of processing power and memory, and may be battery powered, thus requiring that they conserve energy by spending much of their time in sleep mode. A typical model is one where the edge devices generally forma single wireless network in which each end-node communicates directly with its parent node in a hub-and-spoke-style architecture. The parent node may be, e.g., an access point on a gateway or a sub-coordinator which is, in turn, connected to the access point or another sub-coordinator.

Figure 1:
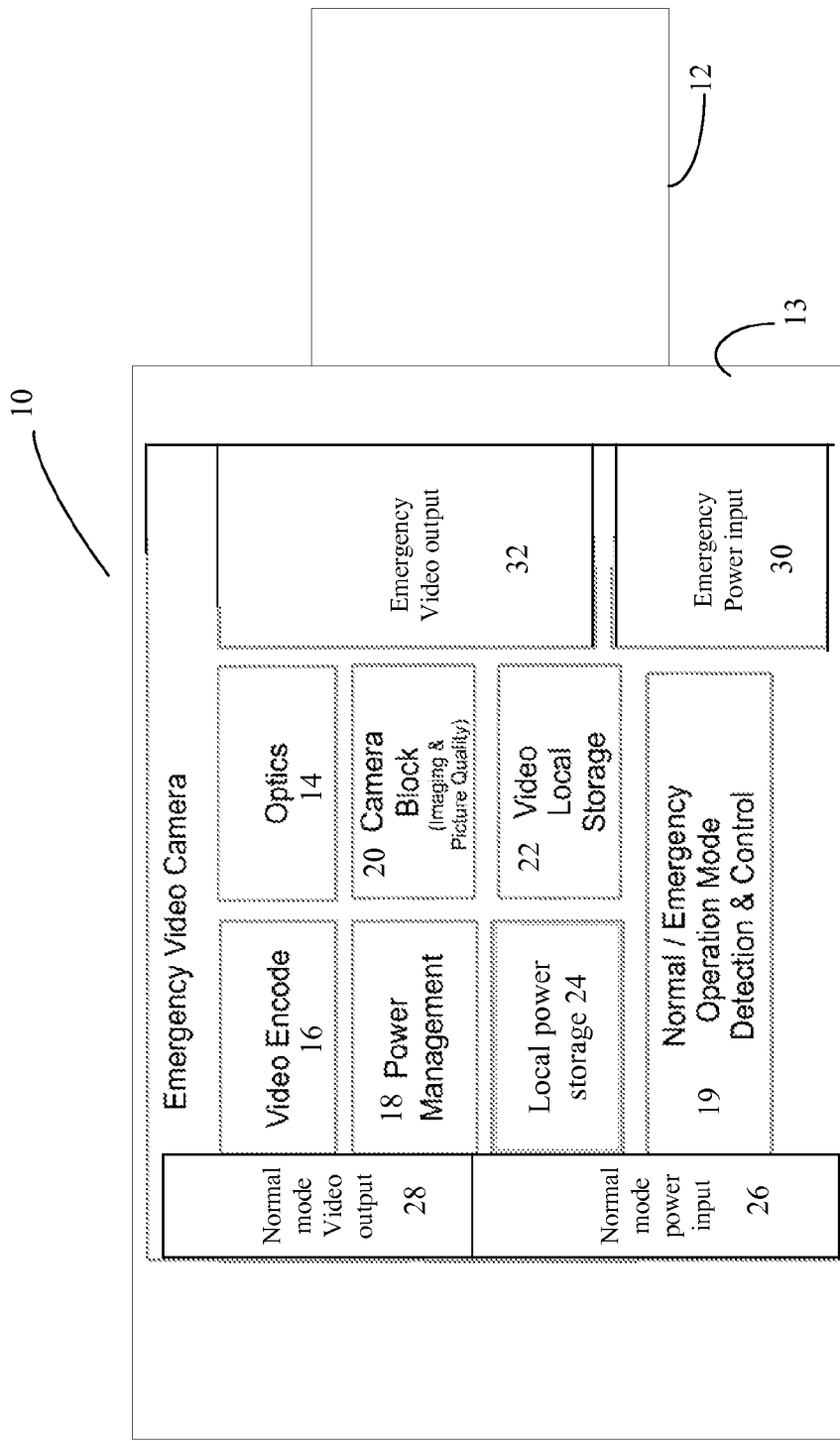
FIG. 1 is a block diagram of an emergency camera element.

Referring now to FIG. 1, an emergency video camera 10 includes a lens 12, a camera body or case 13, optics 14, video encoder 16, power management circuitry 18, camera block circuitry for imaging and picture quality control, 20 and a video local storage device 22. The video camera 10 also includes local power storage 24, e.g., battery backup power. The emergency video camera element operates in a conventional manner with respect to the video encoder, optics, and a camera block circuitry for imaging and picture quality. The emergency video camera element can also include a normal mode power input interface 26 and a normal mode video output interface 28. The emergency video camera element also includes an emergency power input interface 30 and an emergency video output interface 32.

The emergency video output interface 32 is used to convey video data to a central system and can be either wired or wireless (or both). The emergency power input interface is coupled to a source of emergency power and supplies power to the emergency video camera 10 at least during emergency situations, when for example normal building supplied power is shut-off. The emergency video camera 10 includes depending on a specific configuration the normal input power input interface 26, i.e., powered by building power and used during normal operation, and a normal video output interface 28 used during normal operation. The emergency video camera 10 includes a local power storage device to provide a source of power during situations where the building power is unavailable.

Within the emergency video camera 10 either the power management circuitry 18 or other circuitry 19 detects the absence of normal building power (either from the interface 26 or from a signal that is transmitted from a server, indicating that normal building power was lost. The power management circuitry 18 or other circuitry causes the emergency video camera 10 to automatically switch to obtain power from the emergency power input 30 and provide video to emergency video output 32. Alternatively, the emergency video camera 10 senses via a message from the sensor network the loss or imminent loss of power and switches tp emergency power and emergency video output as discussed above.

Figure 2:
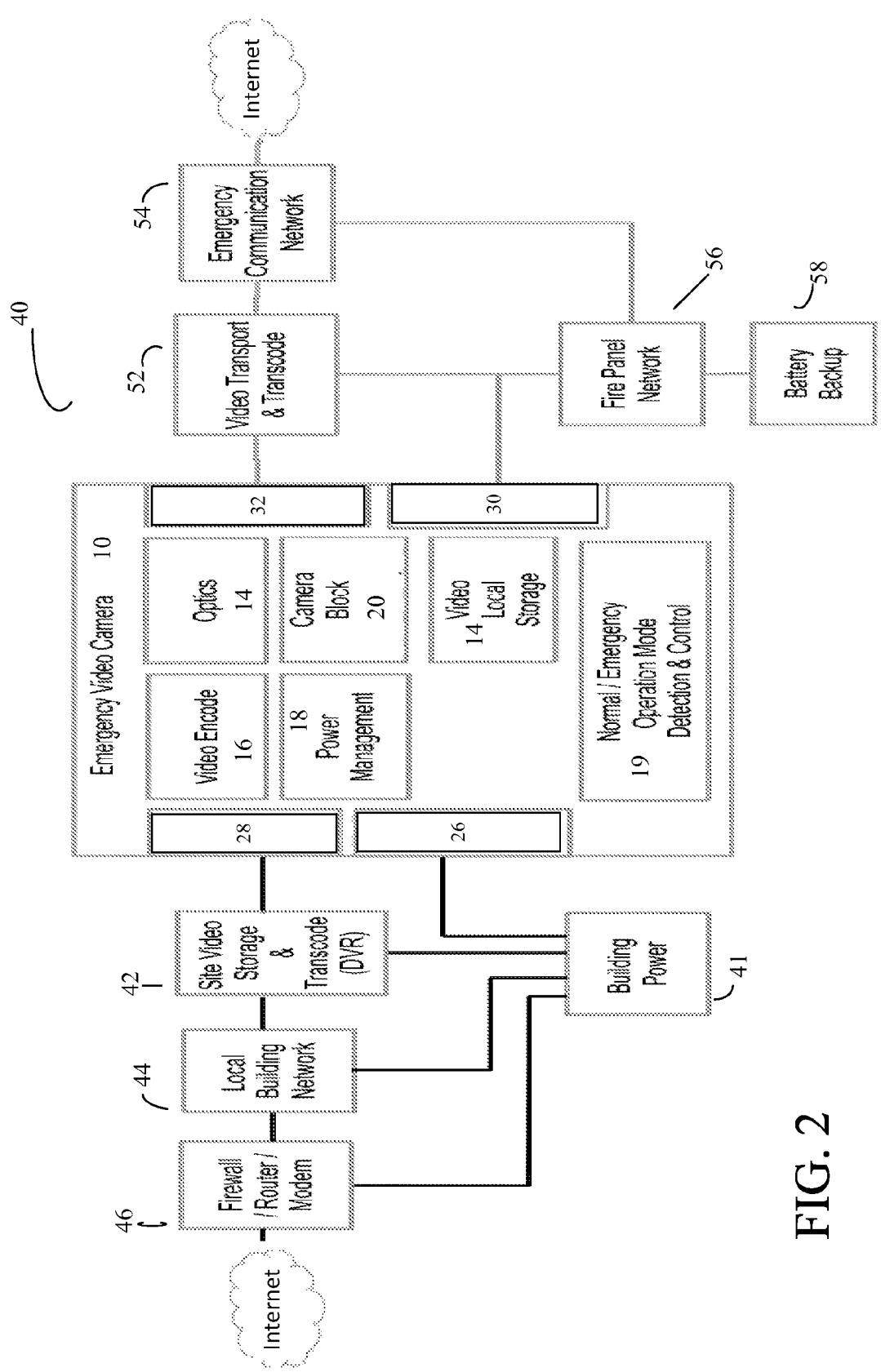
FIGS. 2-5 are block diagrams of a camera system incorporating the emergency camera element of FIG. 1.

Referring now to FIG. 2, in one implementation 40, the emergency video camera 10 contains certain ones of the elements discussed in FIG. 1 that allow the emergency video camera 10 to be connected to a traditional surveillance system for a normal mode of operation using the building communication network and the building power source 41. In this configuration, the emergency video camera element is connected to the Internet, for example, via a site video storage and transport recorder (DVR) 42, a local building network 44, and a firewall and/or router and/or modem 46 out to the Internet or another wide area network (not shown). Within this implementation 40 of the emergency video camera 10, either the power management circuitry 18 or other circuitry detects the absence of normal building power and switches to emergency power and emergency video output or senses via a message from the sensor network the loss or imminent loss of power and switches to emergency power and emergency video output.

The emergency video camera 10 also has an alternate power source to power the camera 10 during a power outage as well as a separate, alternate video transport, transcoding 52 and communications channel 54. The emergency power input interface 30 is coupled to a fire panel network 56 that is fed by a battery backup 58, and the emergency video output interface 32 is coupled to a separate video transport and transcode over a separate network (not shown) that is separate from the local building network 44, i.e., an emergency communications network 54 to the Internet (not shown). The emergency communication network 54 may comprise a number of traditional technologies including wired or wireless communication paths, but physically the emergency communications network 54 is different from the building network 44. The fire panel network 56 also provides power for the video transport and transcode 52, as well as, power for the emergency communication network 54 for communication of video to external monitor devices, e.g., display devices (not shown). Thus, the emergency video camera 10 is configurable for a normal mode of operation using the building network 44 and power 41 but has an alternate configuration that provides the emergency video camera 10 power from the building fire panel 56 and an alternate video transport, transcoding 52 and communications channel 54.

Figure 3:
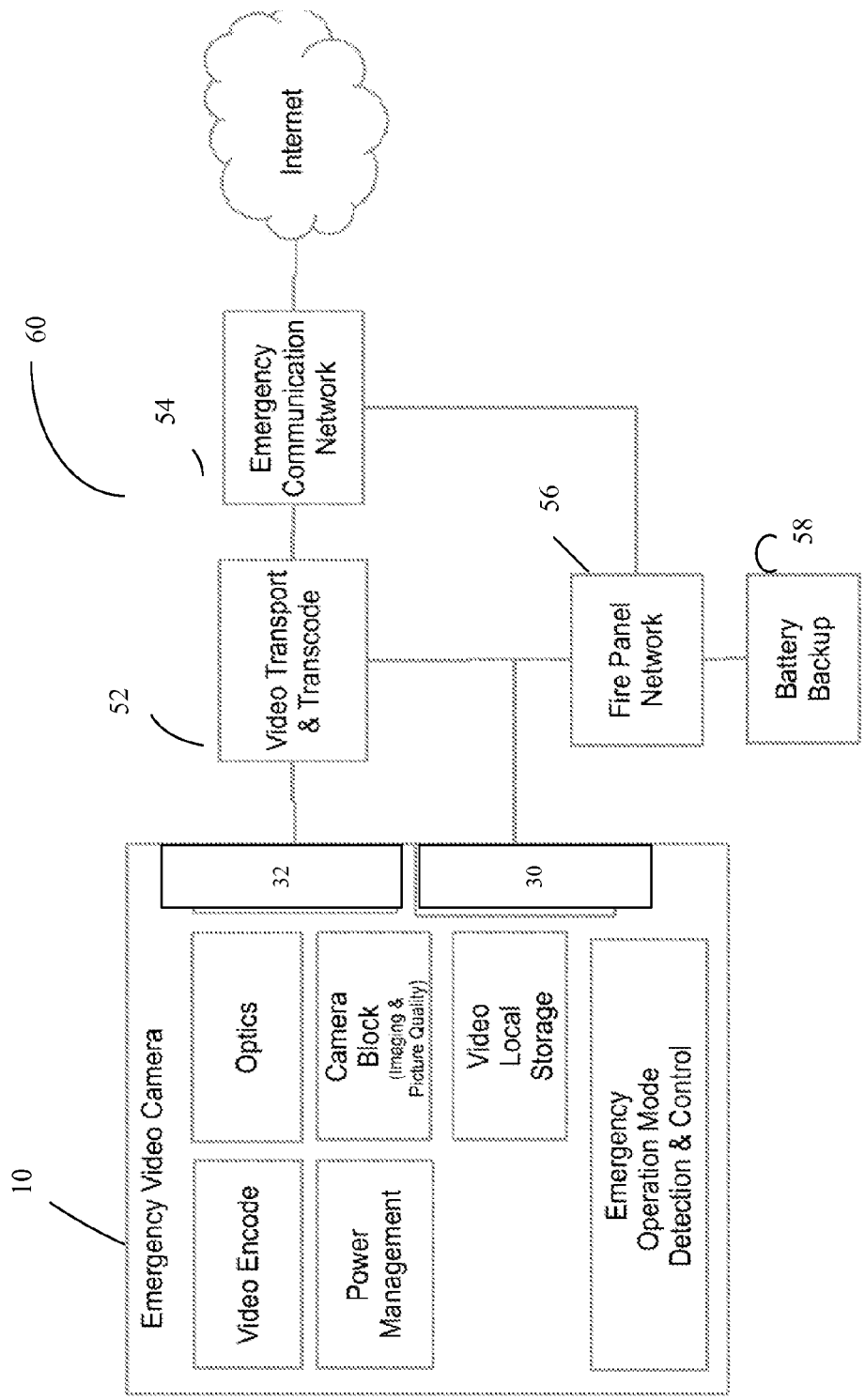

Referring now to FIG. 3, a second implementation 60 has the emergency video camera 10 connected to operate only during emergency conditions. In this implementation 60, the camera 10 is powered by the fire panel network 56 that also provides power for the video transport and transcode 52 as well as power for the emergency communication network 54 for communication of video to the external monitors, via the Internet (or other network, e.g., a wide area network). The emergency communication network 54 may be a number of traditional technologies including wired or wireless communication paths. Within this implementation 60, the emergency video camera 10 will either continuously operate from power from the fire panel or be awaken in absence normal building power and will use emergency power from the fire panel fed to the power interface 30 and emergency video output 32 provide video to the video transport and transcoder 52.

Figure 4:
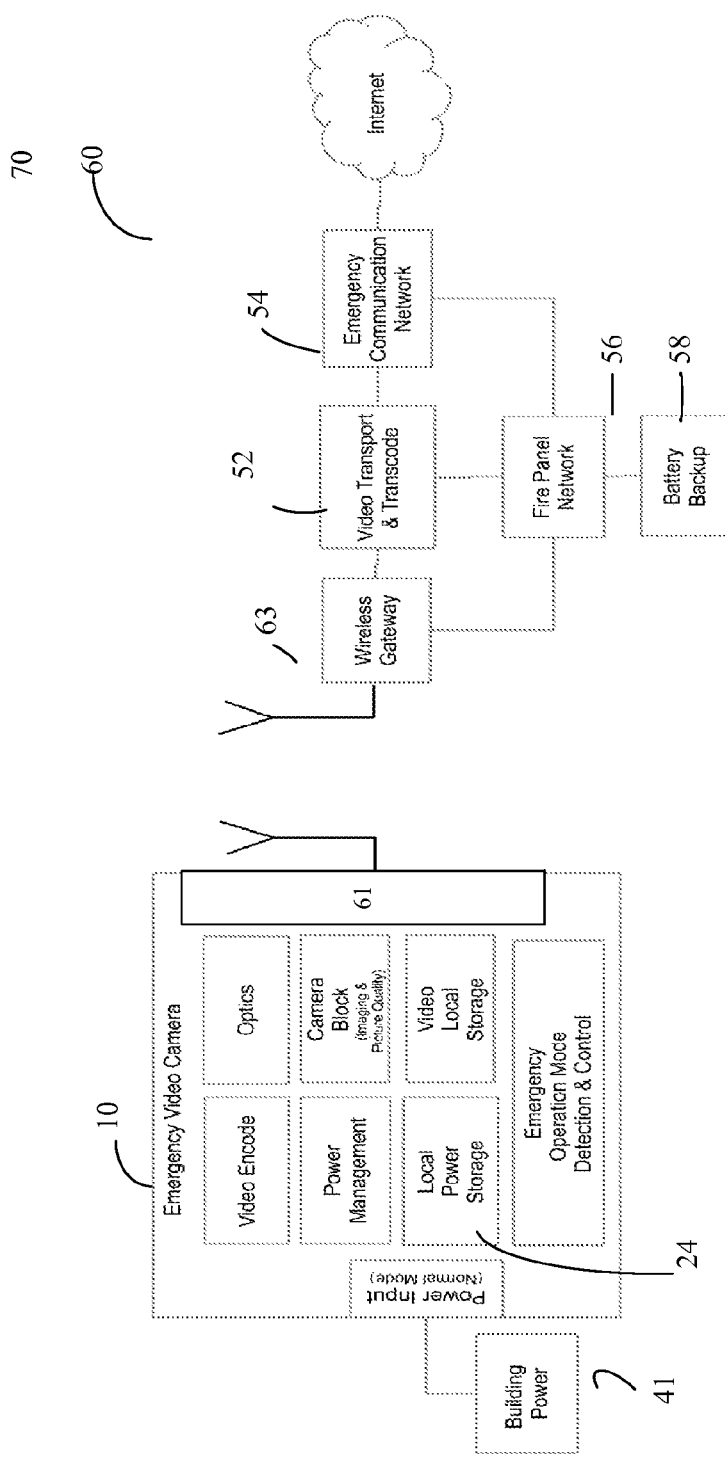

Referring now to FIG. 4, a third implementation 70 has the emergency video camera 10 powered by the building power grid and with the internal, local power storage 24 (e.g., a rechargeable high capacity storage battery or, a supercapacitor, i.e., an electrical double-layer capacitor or pseudocapacitor used for energy storage) to operate for a period of time during a building power outage. This implementation also has a wireless connection 61 to a wireless gateway 63 powered by the fire panel 56 and with battery backup 58. The gateway 63 feeds video transport and transcoder 52 and network 54 to provide video for the external monitors via the Internet.

Figure 5:
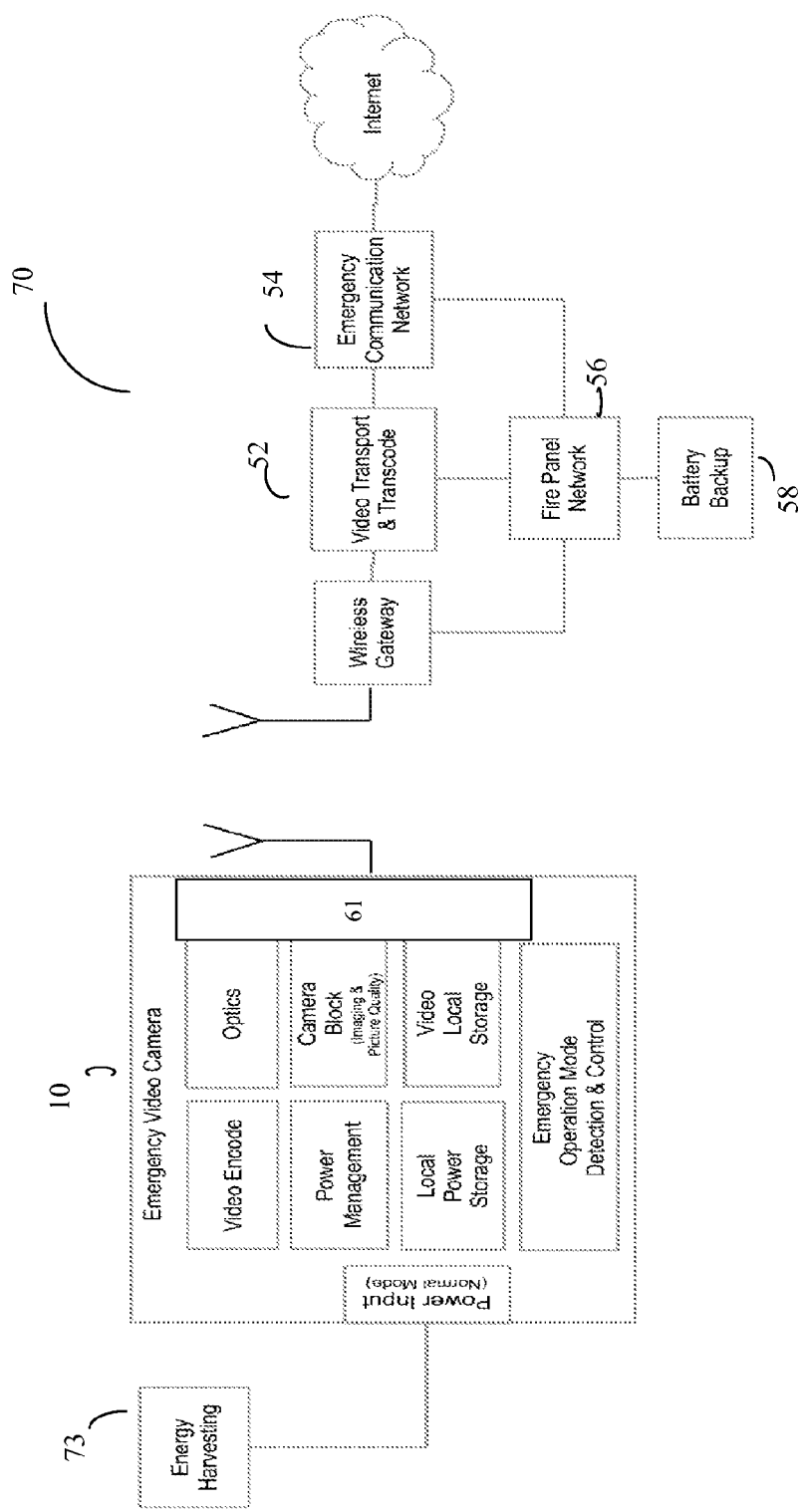

Referring now to FIG. 5, a fourth implementation 70 has the emergency video camera 10 powered by a local energy harvesting element 73 such as a photovoltaic cell that collects energy and stores the energy in local energy storage 24, e.g., a rechargeable high capacity storage battery or by a supercapacitor, i.e., an electrical double-layer capacitor or pseudocapacitor used for energy storage. During an emergency, the emergency video camera 10 is activated, and powered by the energy storage element 24. In this implementation 70, the emergency video camera 10 powered by the local energy harvesting technique that will power the camera 10 during a power outage. Exemplary local energy harvesting techniques include a photovoltaic cell that collects energy and stores energy during normal operation in a rechargeable battery or a supercapacitor 24. This implementation also has a wireless connection 61 to a wireless gateway 63 powered by the fire panel 56 and with battery backup 58. The gateway 63 feeds video transport and transcoder 52 and network 54 to provide video for monitors via the Internet.

The emergency camera system 10 is implemented using any appropriate type of camera optical system and computing device or any other type of intelligent device capable of executing instructions, connecting to a network, and forwarding data packets through the network. Each of processes discussed above may be stored on one or more non-transitory machine-readable media, such as computer memory persistent or non-persistent to store executable instructions. Each of these devices may also include one or more processing devices (e.g., microprocessors, programmable logic, application-specific integrated circuits, and so forth) for executing the instructions to perform all or part of the functions described herein.

Figure 6:
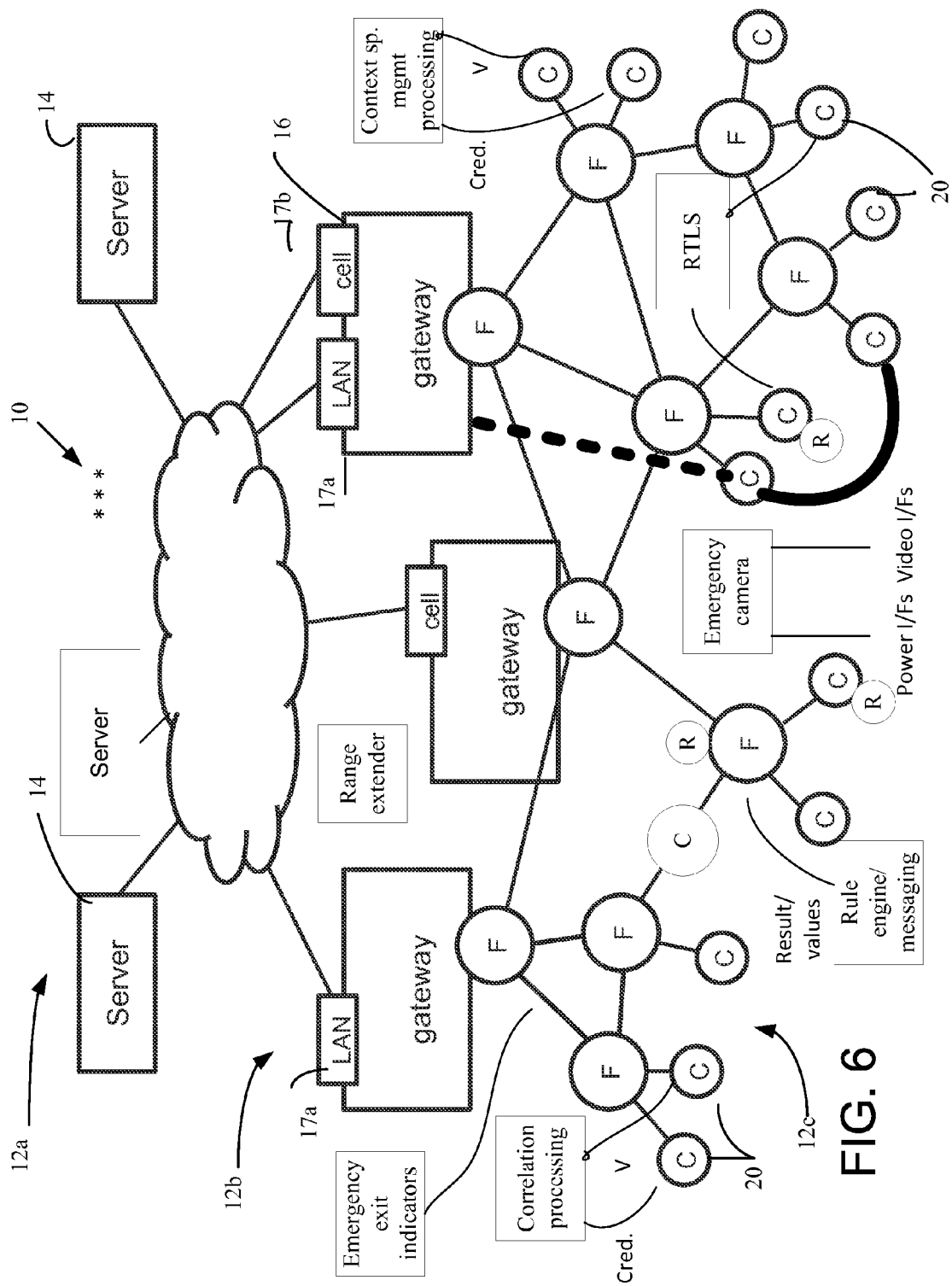
FIG. 6 is a block diagram of components of an example networked security system.

FIG. 6 shows an example of a security system on a Wireless Sensor Network (WSN). In the WSN, the distributed network 10 is logically divided into a set of tiers or hierarchical levels 12a-12c. In an upper tier or hierarchical level 12a of the network are disposed servers and/or virtual servers 14 running a "cloud computing" paradigm that are networked together using well-established networking technology such as Internet protocols or which can be private networks that use none or part of the Internet. Applications that run on those servers 14 communicate using various protocols such as for Web Internet networks XML/SOAP, RESTful web service, and other application layer technologies such as HTTP and ATOM. The distributed network 10 has direct links between devices (nodes) as shown and discussed below.

The distributed network 10 includes a second logically divided tier or hierarchical level 12b, referred to here as a middle tier that involves gateways 16 located at central, convenient places inside individual buildings and structures. These gateways 16 communicate with servers 14 in the upper tier whether the servers are stand-alone dedicated servers and/or cloud based servers running cloud applications using web programming techniques. The middle tier gateways 16 are also shown with both local area network 17a (e.g., Ethernet or 802.11) and cellular network interfaces 17b.

The distributed network topology also includes a lower tier (edge layer) 12c set of devices that involve fully-functional sensor nodes 18 (e.g., sensor nodes that include wireless devices, e.g., transceivers or at least transmitters, which in FIG. 6 are marked in with an "F") as well as constrained wireless sensor nodes or sensor end-nodes 20 (marked in the FIG. 6 with "C"). In some embodiments wired sensors (not shown) can be included in aspects of the distributed network 10.

Constrained computing devices 20 as used herein are devices with substantially less persistent and volatile memory other computing devices, sensors in a detection system. Currently examples of constrained devices would be those with less than about a megabyte of flash/persistent memory, and less than 10-20 kbytes of RAM/volatile memory). These constrained devices 20 are configured in this manner; generally due to cost/physical configuration considerations. These types of constrained devices 20 generally have a static software image (i.e., the logic programmed into the constrained device is always the same).

In a typical network, the edge (wirelessly-connected) tier of the network is comprised of highly resource-constrained devices with specific functions. These devices have a small-to-moderate amount of processing power and memory, and often are battery powered, thus requiring that they conserve energy by spending much of their time in sleep mode. A typical model is one where the edge devices generally form a single wireless network in which each end-node communicates directly with its parent node in a hub-and-spoke-style architecture. The parent node may be, e.g., an access point on a gateway or a sub-coordinator which is, in turn, connected to the access point or another sub-coordinator.

Each gateway is equipped with an access point (fully functional node or "F" node) that is physically attached to that access point and that provides a wireless connection point to other nodes in the wireless network. The links (illustrated by lines not numbered) shown in FIG. 6 represent direct (single-hop network layer) connections between devices. A formal networking layer (that functions in each of the three tiers shown in FIG. 6) uses a series of these direct links together with routing devices to send messages (fragmented or non-fragmented) from one device to another over the network.

The WSN 10 implements a state machine approach to an application layer that runs on the lower tier devices 18 and 20. Discussed below is an example of a particular implementation of such an approach. States in the state machine are comprised of sets of functions that execute in coordination, and these functions can be individually deleted or substituted or added to in order to alter the states in the state machine of a particular tower tier device.

The WSN state function based application layer uses an edge device operating system (not shown, but such as disclosed in the above mentioned provisional application) that allows for loading and execution of individual functions (after the booting of the device) without rebooting the device (so-called "dynamic programming"). In other implementations, edge devices could use other operating systems provided such systems allow for loading and execution of individual functions (after the booting of the device) preferable without rebooting of the edge devices.

As shown in FIG. 6, correlation processing receives inputs from certain constrained nodes (although these can also be fully functional nodes). These inputs may include credential information and video information, and the correlation processing may produce correlated results that are sent over the network. Context management processing receives inputs from certain constrained nodes (although these can also be fully functional nodes) e.g., credential information and video and grouping information, and performs context processing with results sent over the network. The network supports operation of emergency exit indicators; emergency cameras as well as distributed rule processing and rule engine/messaging processing. Range extenders are used with e.g., gateways, and a real time location system receives inputs from various sensors (e.g., constrained type) as shown. Servers interface to the WSN via a cloud computing configuration and parts of some networks can be nm as sub-nets.

The sensors provide in addition to an indication that something is detected in an area within the range of the sensors, detailed additional information that can be used to evaluate what that indication may be without the intrusion detection panel being required to perform extensive analysis of inputs to the particular sensor.

For example, a motion detector could be configured to analyze the heat signature of a warm body moving in a room to determine if the body is that of a human or a pet. Results of that analysis would be a message or data that conveys information about the body detected. Various sensors thus are used to sense sound, motion, vibration, pressure, heat, images, and so forth, in an appropriate combination to detect a true or verified alarm condition at the intrusion detection panel.

Recognition software can be used to discriminate between objects that are a human and objects that are an animal; further facial recognition software can be built into video cameras and used to verify that the perimeter intrusion was the result of a recognized, authorized individual. Such video cameras would comprise a processor and memory and the recognition software to process inputs (captured images) by the camera and produce the metadata to convey information regarding recognition or lack of recognition of an individual captured by the video camera. The processing could also alternatively or in addition include information regarding characteristic of the individual in the area captured/monitored by the video camera. Thus, depending on the circumstances, the information would be either metadata received from enhanced motion detectors and video cameras that performed enhanced analysis on inputs to the sensor that gives characteristics of the perimeter intrusion or a metadata resulting from very complex processing that seeks to establish recognition of the object.

Sensor devices can integrate multiple sensors to generate more complex outputs so that the intrusion detection panel can utilize its processing capabilities to execute algorithms that analyze the environment by building virtual images or signatures of the environment to make an intelligent decision about the validity of a breach.

Memory stores program instructions and data used by the processor of the intrusion detection panel. The memory may be a suitable combination of random access memory, and read-only memory, and may host suitable program instructions (e.g. firmware or operating software), and configuration and operating data and may be organized as a file system or otherwise. The stored program instruction may include one or more authentication processes for authenticating one or more users. The program instructions stored in the memory of the panel may further store software components allowing network communications and establishment of connections to the data network. The software components may, for example, include an internet protocol (IP) stack, as well as driver components for the various interfaces, including the interfaces and the keypad. Other software components suitable for establishing a connection and communicating across network will be apparent to those of ordinary skill.

Program instructions stored in the memory, along with configuration data may control overall operation of the panel.

The monitoring server includes one or more processing devices (e.g., microprocessors), a network interface and a memory (all not illustrated). The monitoring server may physically take the form of a rack mounted card and may be in communication with one or more operator terminals (not shown) that include display devices (not shown). An example monitoring server is a SURGARD™ SG-System III Virtual, or similar system.

The processor of each monitoring server acts as a controller for each monitoring server, and is in communication with, and controls overall operation, of each server. The processor may include, or be in communication with, the memory that stores processor executable instructions controlling the overall operation of the monitoring server. Suitable software enable each monitoring server to receive alarms and cause appropriate actions to occur. Software may include a suitable Internet protocol (IP) stack and applications/clients.

Each monitoring server of the central monitoring station may be associated with an IP address and port(s) by which it communicates with the control panels and/or the user devices to handle alarm events, etc. The monitoring server address may be static, and thus always identify a particular one of monitoring server to the intrusion detection panels. Alternatively, dynamic addresses could be used, and associated with static domain names, resolved through a domain name service.

The network interface card interfaces with the network to receive incoming signals, and may for example take the form of an Ethernet network interface card (NIC). The servers may be computers, thin-clients, or the like, to which received data representative of an alarm event is passed for handling by human operators. The monitoring station may further include, or have access to, a subscriber database that includes a database under control of a database engine. The database may contain entries corresponding to the various subscriber devices/processes to panels like the panel that are serviced by the monitoring station.

All or part of the processes described herein and their various modifications (hereinafter referred to as "the processes") can be implemented, at least in part, via a computer program product, i.e., a computer program tangibly embodied in one or more tangible, physical hardware storage devices that are computer and/or machine-readable storage devices for execution by, or to control the operation of, data processing apparatus, e.g., a programmable processor, a computer, or multiple computers. A computer program can be written in any form of programming language, including compiled or interpreted languages, and it can be deployed in any form, including as a stand-atone program or as a module, component, subroutine, or other unit suitable for use in a computing environment. A computer program can be deployed to be executed on one computer or on multiple computers at one site or distributed across multiple sites and interconnected by a network.

Actions associated with implementing the processes can be performed by one or more programmable processors executing one or more computer programs to perform the functions of the calibration process. All or part of the processes can be implemented as, special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks.

Tangible, physical hardware storage devices that are suitable for embodying computer program instructions and data include all forms of non-volatile storage, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks and volatile computer memory, e.g., RAM such as static and dynamic RAM, as well as erasable memory, e.g., flash memory.

In addition, the logic flows depicted in the figures do not require the particular order shown, or sequential order, to achieve desirable results. In addition, other actions may be provided, or actions may be eliminated, from the described flows, and other components may be added to, or removed from, the described systems. Likewise, actions depicted in the figures may be performed by different entities or consolidated.

Elements of different embodiments described herein may be combined to form other embodiments not specifically set forth above. Elements may be left out of the processes, computer programs, Web pages, etc. described herein without adversely affecting their operation. Furthermore, various separate elements may be combined into one or more individual elements to perform the functions described herein.

Other implementations not specifically described herein are also within the scope of the following claims.

What is claimed is:

1. A camera system comprises:
a camera comprising optical components to capture and process optical energy to produce images, camera processing circuitry that receives the optical energy and processes the optical energy into electrical signals and encodes the signals into a defined format;
power management circuitry to power the camera system, the power management system comprising;
a first power interface configured to couple to normal building supplied power;
a second, different power interface configured to connect to a fire panel, with the second different power interface receiving power from the fire panel to power the camera system during emergency operations; and
circuitry that receives a signal that causes the circuitry to switch from the first power interface to the second power interface upon detection of loss or imminent loss of power from the first interface.

2. The system of claim 1 further comprising a video local storage device.

3. The system of claim 1 further comprising:
a local power storage device that supplies power to the camera when normal building supplied power or fire panel supplied power is unavailable.

4. The system of claim 1 wherein the signal that causes the circuitry to switch is sent from a server.

5. The system of claim 1 further comprising:
a first video output interface for transport of video data during normal operation over a building communication network powered from building power; and
a second different video output interface for transport of video over a network separate from the local building communications network to the Internet, with the second different video output interface powered by the second power interface.

6. A camera system comprises:
a camera comprising optical components to capture and process light to produce images, camera processing circuitry that receives the light and processes the light into electrical signals and encodes the signals into a defined format;
a fire panel that receives power during emergency operations, the fire panel having a device that supplies backup power;
power management circuitry to manage power for the camera system;
a first power interface configured to couple to normal building supplied power;
a second, different power interface connected to the fire panel, with the second different power interface receiving power from the fire panel to power the camera system during emergency operations;
a first video output interface; and
a second, different video output interface that is coupled to a second, different communications network that is physically separate from the first communication network and
circuitry to switch from the first power interface to the second power interface and to provide video to the second, different video output interface upon reception of a signal transmitted from a server indicating that normal building power was lost.

7. The system of claim 6 further comprising a video local storage device.

8. The system of claim 6 further comprising at one of the first and second output interfaces, circuitry for providing a wireless network connection to the camera.

9. The system of claim 6 wherein the first video output interface is a normal video output interface for transport of video over a building communication network powered from building supplied power during non-emergency operation, and the second, different video output interface is an emergency video output interface for transport of video over a wireless network separate from the local building communications network to the Internet, the second, different video output interface comprising a wireless connection to a wireless gateway.

10. A surveillance system comprises:
a fire panel including a local power storage element to provide backup power;
one or more camera systems comprising:
a camera element comprising optical components to capture and process light to produce images, camera processing circuitry that receives the light and processes the light into electrical signals and encodes the signals into a defined format; and, with at least one of the camera systems further comprising:
power management circuitry to power the at least one of the camera systems, the power management system comprising;
a first power interface connected to normal building supplied power;
a second, different power interface connected through a backup power network that is coupled to the fire panel, and which receives power from the fire panel during emergency operation;
circuitry to switch from providing power to the at least one camera system from the first power interface of the at least one camera system to the second power interface of the at least one camera system in response to a signal received from either a server system or generated by the circuitry upon detection of loss or imminent loss of normal building supplied power from the first interface;
a first video output interface that is coupled to a first communications network; and
a second, different video output interface that is coupled to a second, different communications network that is physically separate from the first communication network.

11. The system of claim 10 wherein the local power storage element supplies power to the camera only during emergencies.

12. The system of claim 11 wherein the local power storage element is fed by a power harvesting element that supplies power to the local storage element.

13. The system of claim 11 wherein the local power storage element is charged by building power.

14. The system of claim 10 further comprising:
sensor nodes; and
a wireless sensor network to couple the one or more video cameras to monitors and the sensor nodes to monitoring units.

15. A camera system comprises:
a camera comprising optical components to capture and process optical energy to produce images, camera processing circuitry that receives the optical energy and processes the optical energy into electrical signals and encodes the signals into a defined format;
a local power storage device that supplies power to the camera;
power management circuitry to power the camera system, the power management system comprising;
a first power interface configured to connect to normal building supplied power;
a second, different power interface coupled to the local power storage element to provide backup power to the camera;
a third, different power interface configured to connect to a fire panel, with the second different power interface receiving power from the fire panel to power the camera system during emergency operations; and
circuitry that receives a signal corresponding to a detection of loss or imminent loss of normal building power, to switch powering of the camera system from receiving power at either the first power interface or the second power interface to the third power interface.

16. The system of claim 15 wherein the local power storage device supplies power to the camera when normal building supplied power or fire panel supplied power is unavailable.

17. The system of claim 15 further comprising:
a first video output interface for transport of video data during normal operation over a building communication network powered from building power;
a second different video output interface for transport of video over a network separate from the local building communications network; and
wherein the circuitry is further configured to provide video to the second, different video output interface upon reception of the signal.

18. The system of claim 15 wherein the signal received by the circuitry is received from a server computer.

19. The system of claim 15 wherein the local power storage device is selected from a rechargeable high capacity storage battery or a supercapacitor or a pseudocapacitor.

* * * * *